(12) United States Patent
Crowley

(10) Patent No.: US 6,289,229 B1
(45) Date of Patent: Sep. 11, 2001

(54) READABLE PROBE ARRAY FOR IN VIVO USE

(75) Inventor: Robert J. Crowley, Sudbury, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/233,409

(22) Filed: Jan. 19, 1999

Related U.S. Application Data

(60) Provisional application No. 60/071,906, filed on Jan. 20, 1998.

(51) Int. Cl.$^7$ .................................................. A61B 5/00
(52) U.S. Cl. ...................... 600/310; 600/407; 600/476; 600/312; 600/317; 600/478; 604/19; 604/20; 604/21; 604/22; 604/35; 604/36; 422/82.05; 422/82.06; 422/82.11; 436/86; 436/87; 436/88; 436/89; 435/172; 435/173
(58) Field of Search .................... 600/310, 407, 600/476, 309, 312, 317, 322, 329, 341, 342, 433, 435, 437, 439, 478, 101, 137; 604/19, 20, 21, 22, 37, 27, 35, 36; 422/82.05, 82.06, 82.07–82.09, 82.11; 436/86–89; 435/173, 172

(56) References Cited

U.S. PATENT DOCUMENTS

| | | | |
|---|---|---|---|
| 2,002,559 | 5/1935 | Wappler | 174/83 |
| 2,582,937 | 1/1952 | Fossati | 128/4 |
| 3,176,114 | 3/1965 | Kneisley | 219/223 |
| 4,233,493 | 11/1980 | Nath | 219/354 |
| 4,274,706 | 6/1981 | Tangonan | 350/96.19 |

(List continued on next page.)

FOREIGN PATENT DOCUMENTS

| | | |
|---|---|---|
| 888727 | 7/1953 | (DE) . |
| 3023130 | 1/1982 | (DE) . |
| 4005743 | 2/1990 | (DE) . |
| 19512518 | 4/1995 | (DE) . |
| 0 304 321 | 2/1989 | (EP) . |
| 0314937 | 5/1989 | (EP) . |

(List continued on next page.)

OTHER PUBLICATIONS

Anidjar, et al., "Ultraviolet Laser–Induced Autoflourescence Distinction Between Malignant and Normal Urothelial Cells and Tissues," *J. of Boimed. Optics* 1(3), 335–341 (Jul. 1996).

Bollinger, et al., "LESIT Project 4.04—Integrated UV Sensor," internet publication (1995).

Coleman, et al., "Acoustic Emission and Sonoluminescence Due to Cavitation at the Beam Focus of an Electrohydraulic Shock Wave Lithotripter," *Ultrasound in Med. & Biol.* 18(3), 267,281 (1992).

(List continued on next page.)

*Primary Examiner*—Marvin M. Lateef
*Assistant Examiner*—Jeoyuh Lin
(74) *Attorney, Agent, or Firm*—Testa, Hurwitz & Thibeault, LLP

(57) ABSTRACT

A disposable high density optically readable polydeoxynucleotide array with integral fluorescence excitation and fluorescence emission channels is described. The compact array size allows integration into several types of interventional devices such as catheters, guidewires, needles, trocars and may be used intraoperatively. Highly sensitive monitoring of the metabolic and disease pathways of cells in vivo under varying chemical, genetic and environmental conditions is afforded.

24 Claims, 7 Drawing Sheets

U.S. PATENT DOCUMENTS

| | | | |
|---|---|---|---|
| 4,289,966 | 9/1981 | Roberts | 250/378 |
| 4,340,307 | 7/1982 | Diamond et al. | 356/418 |
| 4,472,728 | 9/1984 | Grant et al. | 357/30 |
| 4,541,272 | 9/1985 | Bause | 73/118 |
| 4,548,505 | 10/1985 | Ono | 356/445 |
| 4,560,286 | 12/1985 | Wickersheim | 374/131 |
| 4,566,057 | 1/1986 | Hinima et al. | 128/303.1 |
| 4,570,638 | 2/1986 | Stoddart et al. | 128/665 |
| 4,578,061 | 3/1986 | Lemelson | 604/164 |
| 4,672,972 | 6/1987 | Berke | 128/653 |
| 4,718,417 | 1/1988 | Kittrell et al. | 128/303.1 |
| 4,803,992 | 2/1989 | Lemelson | 128/634 |
| 4,813,790 | 3/1989 | Frankel et al. | 374/208 |
| 4,832,034 * | 5/1989 | Pizziconi et al. | 128/632 |
| 4,872,458 | 10/1989 | Kanshira et al. | 128/401 |
| 4,882,623 | 11/1989 | Uchikubo | 358/98 |
| 4,894,547 | 1/1990 | Leffell et al. | 250/461.2 |
| 4,895,156 | 1/1990 | Schulze | 128/634 |
| 4,898,175 | 2/1990 | Noguchi | 128/634 |
| 4,902,896 | 2/1990 | Fertig, Sr. et al. | 250/340 |
| 4,925,268 | 5/1990 | Iyer et al. | 350/96.29 |
| 4,928,172 | 5/1990 | Uehara et al. | 358/98 |
| 4,930,516 | 6/1990 | Alfano et al. | 128/435 |
| 4,938,602 | 7/1990 | May et al. | 356/435 |
| 4,981,138 | 1/1991 | Deckelbaum et al. | 128/665 |
| 5,000,901 * | 3/1991 | Iyer et al. | 264/299 |
| 5,001,556 | 3/1991 | Nakamura et al. | 358/98 |
| 5,009,655 | 4/1991 | Diagnault, Jr. et al. | 606/7 |
| 5,021,888 | 6/1991 | Kondou et al. | 358/213.11 |
| 5,034,010 | 7/1991 | Kittrell et al. | 606/15 |
| 5,036,853 | 8/1991 | Jeffcoat et al. | 128/634 |
| 5,042,494 | 8/1991 | Alfano | 128/665 |
| 5,045,056 | 9/1991 | Behl | 604/49 |
| 5,056,503 | 10/1991 | Nagasaki et al. | 128/6 |
| 5,062,428 | 11/1991 | Chance | 128/664 |
| 5,106,387 | 4/1992 | Kittrell et al. | 606/15 |
| 5,115,137 | 5/1992 | Andersson-Engels | 250/461.2 |
| 5,116,759 | 5/1992 | Klainer et al. | 435/288 |
| 5,125,404 | 6/1992 | Kittrell et al. | 128/634 |
| 5,127,407 | 7/1992 | Tan | 128/633 |
| 5,131,398 | 7/1992 | Alfano et al. | 128/665 |
| 5,166,755 | 11/1992 | Gat | 356/419 |
| 5,172,693 | 12/1992 | Doody | 128/633 |
| 5,174,297 | 12/1992 | Daikuzono | 128/665 |
| 5,187,572 | 2/1993 | Nakamura et al. | 358/98 |
| 5,187,672 | 2/1993 | Chance et al. | 364/550 |
| 5,193,542 | 3/1993 | Missanelli et al. | 128/633 |
| 5,197,470 | 3/1993 | Helfer et al. | 128/634 |
| 5,201,318 | 4/1993 | Rava et al. | 128/665 |
| 5,206,174 | 4/1993 | Gehrke et al. | 436/58 |
| 5,213,569 | 5/1993 | Davis | 604/22 |
| 5,233,621 | 8/1993 | Lawandy | 372/22 |
| 5,242,437 | 9/1993 | Everett et al. | 606/15 |
| 5,261,410 | 11/1993 | Alfano et al. | 128/664 |
| 5,262,645 | 11/1993 | Lambert | 250/339 |
| 5,304,173 | 4/1994 | Kittrell et al. | 606/15 |
| 5,305,748 | 4/1994 | Wilk | 128/653.1 |
| 5,309,907 | 5/1994 | Fang et al. | 128/633 |
| 5,318,024 | 6/1994 | Kittrell et al. | 128/634 |
| 5,348,018 | 9/1994 | Alfano et al. | 128/665 |
| 5,350,375 | 9/1994 | Deckelbaum et al. | 606/7 |
| 5,351,532 | 10/1994 | Hager | 73/153 |
| 5,377,676 | 1/1995 | Vari et al. | 128/634 |
| 5,383,467 | 1/1995 | Auer et al. | 128/644 |
| 5,386,827 | 2/1995 | Chance et al. | 128/633 |
| 5,398,844 | 3/1995 | Zaslausky et al. | 221/208 |
| 5,402,778 | 4/1995 | Chance | 128/633 |
| 5,402,792 | 4/1995 | Kimura | 128/663.01 |
| 5,402,801 | 4/1995 | Taylor | 128/898 |
| 5,405,369 | 4/1995 | Selman et al. | 607/88 |
| 5,408,998 | 4/1995 | Mersch | 128/633 |
| 5,413,108 | 5/1995 | Alfano | 128/665 |
| 5,417,207 | 5/1995 | Young et al. | 128/634 |
| 5,417,210 | 5/1995 | Funda et al. | 128/653.1 |
| 5,419,323 | 5/1995 | Kittrell et al. | 128/653.1 |
| 5,421,337 | 6/1995 | Richards-Kortum | 128/665 |
| 5,421,339 | 6/1995 | Ramanujam et al. | 128/665 |
| 5,445,608 | 8/1995 | Chen et al. | 604/20 |
| 5,445,934 | 8/1995 | Fodor et al. | 435/6 |
| 5,452,723 | 9/1995 | Wu et al. | 128/664 |
| 5,456,252 | 10/1995 | Vari et al. | 128/633 |
| 5,461,229 | 10/1995 | Sauter et al. | 250/253 |
| 5,467,767 | 11/1995 | Alfano et al. | 128/665 |
| 5,512,757 | 4/1996 | Cederstrand et al. | 250/373 |
| 5,517,313 | 5/1996 | Colvin, Jr. | 356/417 |
| 5,517,997 | 5/1996 | Fontenot | 128/994 |
| 5,540,691 | 7/1996 | Elstrom et al. | 606/64 |
| 5,542,928 | 8/1996 | Evans et al. | 604/113 |
| 5,545,897 | 8/1996 | Jack | 250/339.13 |
| 5,553,614 | 9/1996 | Chance | 128/633 |
| 5,555,885 | 9/1996 | Chance | 128/654 |
| 5,556,421 | 9/1996 | Prutchi et al. | 607/36 |
| 5,562,100 | 10/1996 | Kittrell et al. | 128/665 |
| 5,571,152 | 11/1996 | Chen et al. | 607/92 |
| 5,579,773 | 12/1996 | Vo-Dinh et al. | 128/665 |
| 5,596,988 | 1/1997 | Markle et al. | 128/635 |
| 5,626,139 | 5/1997 | Szeles et al. | 128/664 |
| 5,632,740 | 5/1997 | Koch et al. | 606/4 |
| 5,636,612 * | 6/1997 | Mitsuhashi et al. | 435/6 |
| 5,647,368 | 7/1997 | Zeng et al. | 128/665 |
| 5,679,512 * | 10/1997 | Laney et al. | 435/6 |
| 5,690,894 * | 11/1997 | Pinkel et al. | 422/68.1 |
| 5,730,134 | 3/1998 | Dumoulin et al. | 128/653.1 |
| 5,769,791 | 6/1998 | Benaron et al. | 600/473 |
| 5,785,658 | 7/1998 | Benaron et al. | 600/473 |
| 5,800,478 | 9/1998 | Chen et al. | 607/88 |
| 5,807,261 | 9/1998 | Benaron et al. | 600/473 |
| 5,829,878 | 11/1998 | Weiss et al. | 374/163 |
| 5,861,253 * | 1/1999 | Asgari et al. | 435/6 |
| 5,885,293 | 3/1999 | McDevitt | 606/80 |
| 5,928,137 | 7/1999 | Green | 600/160 |
| 5,935,119 * | 8/1999 | Guy et al. | 604/500 |
| 6,008,014 * | 12/1999 | Gimeno et al. | 435/69.1 |

FOREIGN PATENT DOCUMENTS

| | | | |
|---|---|---|---|
| 0629380 | 12/1994 | (EP) . | |
| 0650694 | 5/1995 | (EP) . | |
| 0728440 | 8/1996 | (EP) . | |
| 0777119 | 6/1997 | (EP) . | |
| 0792618 | 9/1997 | (EP) . | |
| 0 920 831 | 6/1999 | (EP) . | |
| 2/223828 | 9/1990 | (JP) . | |
| 7/88105 | 4/1995 | (JP) . | |
| 7-289506 | 11/1995 | (JP) . | |
| 8-83569 | 3/1996 | (JP) . | |
| 9-192138 | 9/1997 | (JP) . | |
| WO 90/04352 | 5/1990 | (WO) | A61B/5/00 |
| WO 90/12536 | 11/1990 | (WO) | A61B/5/00 |
| WO 91/15151 | 10/1991 | (WO) | A61B/5/00 |
| WO 92/14514 | 9/1992 | (WO) | A61N/5/06 |
| WO 92/15253 | 9/1992 | (WO) | A61B/17/22 |
| WO 93 18186 | 9/1993 | (WO) . | |
| WO 94/13191 | 6/1994 | (WO) | A61B/1/06 |
| WO 95/12349 | 5/1995 | (WO) | A61B/5/00 |
| WO 96/05693 | 2/1996 | (WO) | H04N/1/48 |
| WO 96/06946 | 3/1996 | (WO) . | |
| WO 96/07451 | 3/1996 | (WO) | A61N/5/06 |
| WO 96/24406 | 8/1996 | (WO) | A61N/5/06 |
| WO 96/39932 | 12/1996 | (WO) | A61B/5/05 |
| WO97/01985 | 1/1997 | (WO) | A61B/5/00 |
| WO 98/22805 | 5/1998 | (WO) | G01N/21/258 |

OTHER PUBLICATIONS

Cothren et al., "Gastrointestinal Tissue Diagnosis by Laser–Induced Flourescence Spectroscopy at Endoscopy," *Gastrointestinal Endoscopy* 36(2) 105–111 (1990).

Crowley et al., "Ultrasound Guided Therapeutic Catheters: Recent Developments and Clinical Results," *Int'l Journal of Cardiac Imaging* 6 145–156 (1991).

Huang et al., "Flourescence Diagnosis of Gynecological Cancerous and Normal Tissues," *SPIE 2135* 42–45 (1994).

Kapadia, et al., "Laser–Induced Fluorescence Spectroscopy of Human Colonic Muscosa,"*Gastroenterology* 99(1) 150–157 (190).

Ko, "Biomedical Sensors and Acuators," *Electronics in Medicine and Biology* 26–53–26–68 (1989).

Kopp, et al., "Stay Tuned: Photonic Filters Color Your World," *Photonics Spectra* 125–129 (Mar. 1997).

Lilge, et al., "Light Induced Fluorescence Spectroscopy at Endoscopy" *Presented at the 10th Asian Pacific Congress on Gastroenterology.*

Meindl, "Implantable Telemetry in Biomedical Research," *Electronics in Medicine and Biology* 26–41–26–52 (1989).

Petrofsky, "In Vivo Measurement of Brain Blood Flow in the Cat," *IEEE Transactions on Biomed. Eng.* 26(8) 441–445 (Aug. 1979).

Vona, et al., "A Test of the Hypothesis That Caviation at the Focal Area of an Extracorporeal Shock Wave Lithotripter Produces Far Ultraviolet and Soft X–ray Emissions," *J. Acoust. Soc. Am.* 98(2) 706–710 (Aug. ).

International Search Report, PCT/US97/20324 (Mar. 11, 1998).

International Search Report, PCT/US97/20367 (Mar. 23, 1998).

International Search Report, PCT/US97/20435 (May 19, 1998).

International Search Report, PCT/US98/20019 (Jan. 20, 1999).

International Search Report, PCT/US98/20018 (Jan. 21, 1999).

International Search Report, PCT/US98/21100 (Feb. 8, 1999).

* cited by examiner

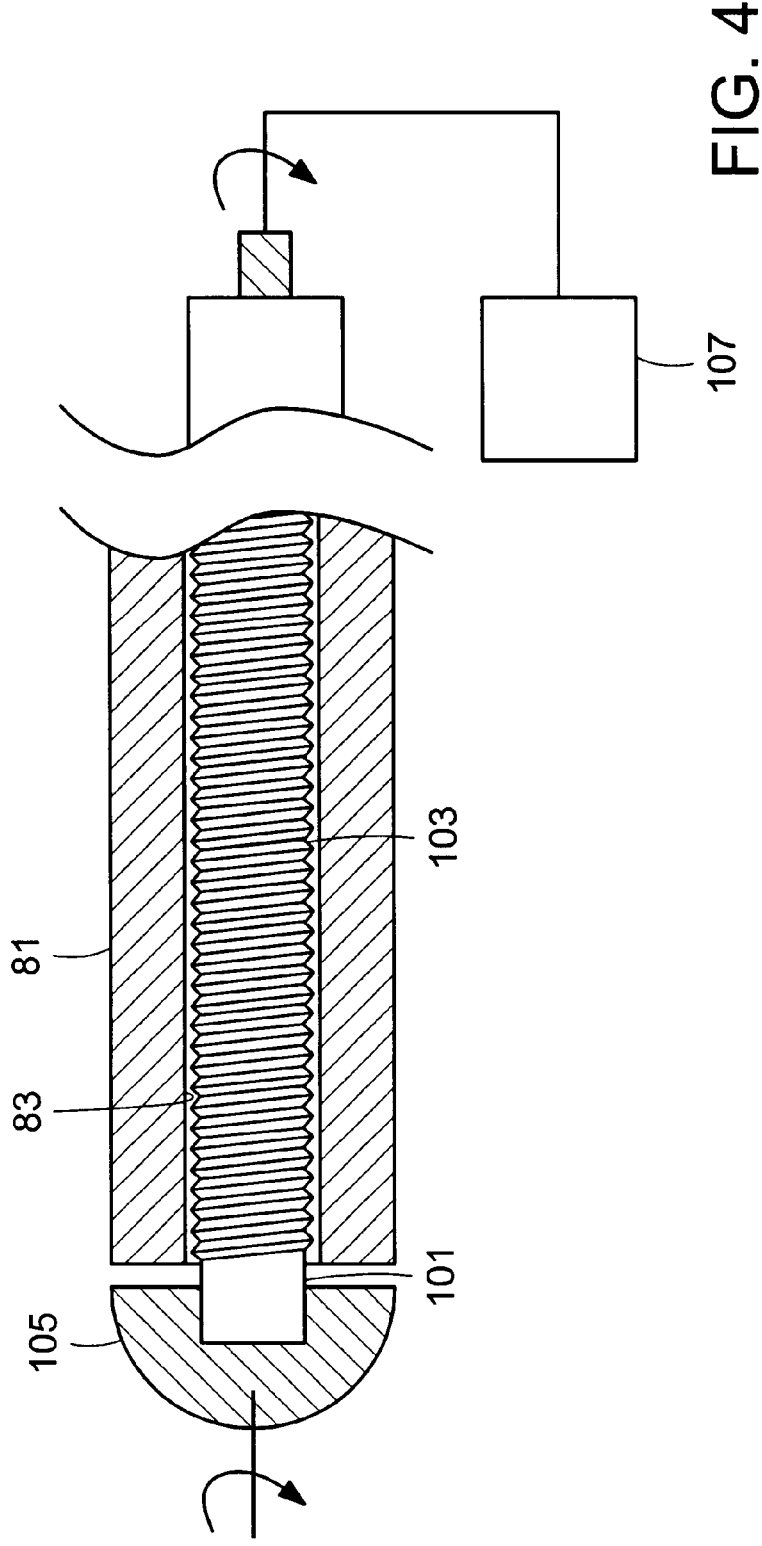

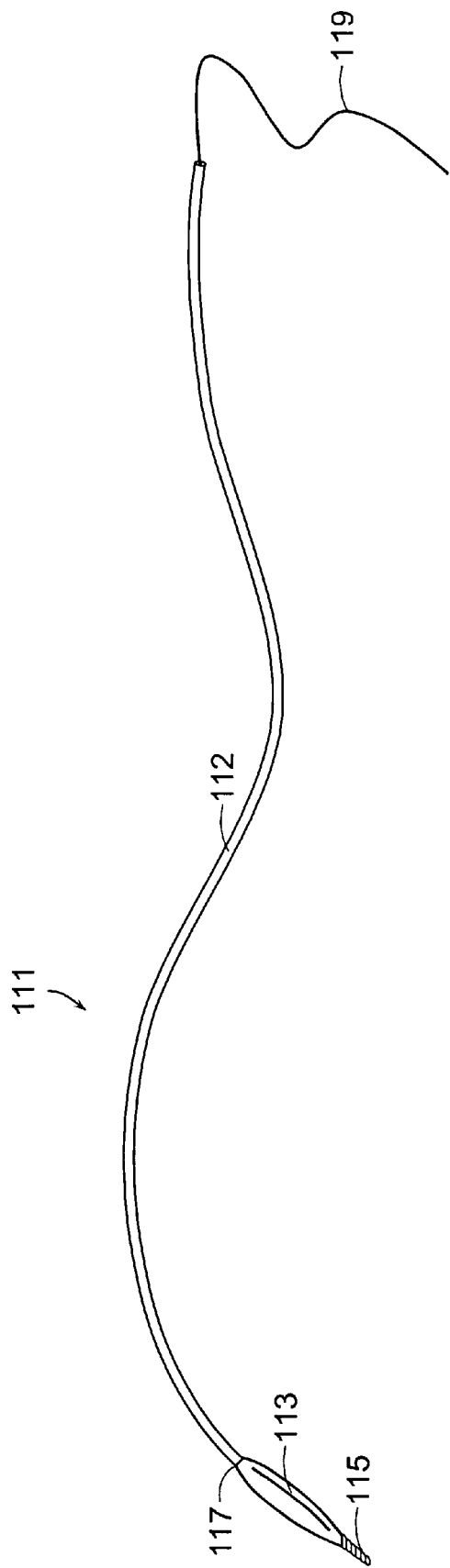

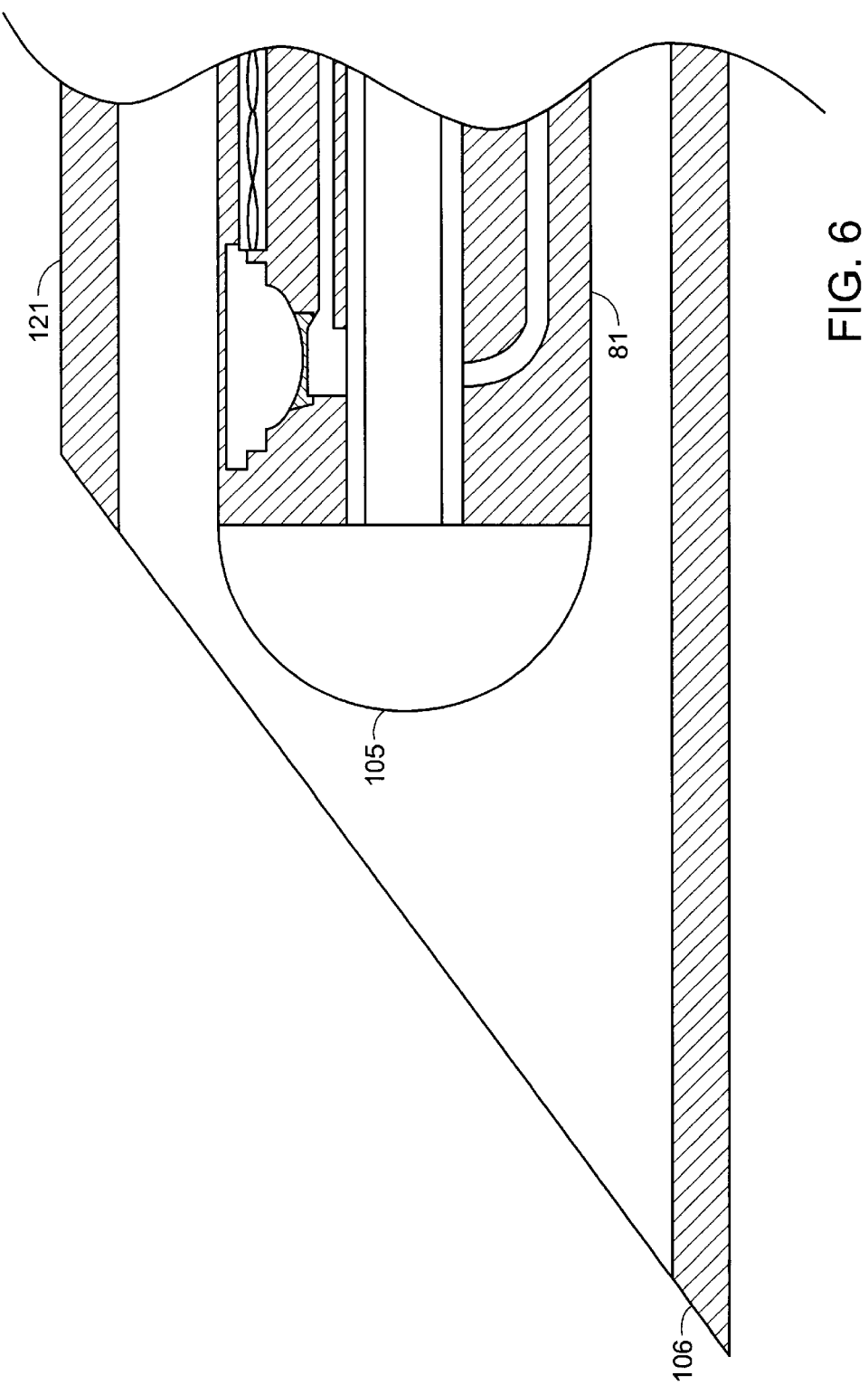

READABLE PROBE ARRAY FOR IN VIVO USE

RELATED APPLICATIONS

This application claims priority under 35 U.S.C. § 119(e) to application Ser. No. 60/071,906, filed Jan. 20, 1998.

BACKGROUND OF THE INVENTION

Polydeoxynucleotide and oligonucleotide sequencing with laboratory-based instruments has become inexpensive and reliable due to the variety and availability of complimentary fluorescent labeled target sequences. These fluorescent labeled probes may be specially tailored to hybridize with genomic DNA segments and form base pair matches that can accurately detect the presence of inherited genetic disorders or native-cell mutations. Under excitation light in the visible or UV range, the associated fluorescent marker attached to the probe emits a secondary emission which may be detected by a charge-coupled device (CCD) array, photodiode, or other spectrally sensitive light detector.

However, current techniques require the use of specialized reagents and additional processing to separate the cell wall and other components before analysis. The analyte is removed and introduced into an assay chamber for analysis. The chambers are housed in portable or tabletop analytic instruments that typically contain an excitation source, detection sensors, spatial reading or imaging devices, and archiving capabilities. These systems are expensive and require that tissue samples be processed prior to use. The biggest drawback to these types of systems is their inherent inability to perform fast, localized reading of array probes in a convenient, and repeatable manner in vivo. In vivo monitoring and detection of changes to the human body in response to therapy is needed to expedite trials and to monitor results from therapy, and would allow doctors to treat serious diseases such as cancer safely in a more effective and less costly manner.

SUMMARY OF THE INVENTION

The present invention performs specific detection and analysis of biological analytes in vivo using a simplified, low cost set of components. In one embodiment the small size and simplified operation allows the entire device to be housed in a catheter. In one aspect, the device consists of a housing, a light excitation source, and detector and at least one fluorescent labeled probe material on a substrate that is exposed to the tissue of the body. The excitation source may be directed at the substrate carrying the probe, or may be a conductor of the excitation energy. Other embodiments include the use of a lumen to introduce a lysing agent or energy to the area of interest. The lysing agent or energy may be an ultrasonic transducer capable of rupturing cell membranes through the use of a brief burst of ultrasonic energy. In another aspect, a lysing system is used in which pressurization and evacuation of the sample via the lumen adjacent to the probe array creates a pressure capable of rupturing the cell membrane. Each of the probes may be read by application of electrical current to the excitation source and by detecting the presence or absence of signal via the probe sensor. The probe sensor may be a photodiode that is responsive to light emitted by the fluorescent probe material. Two probes may be mixed and read by two sensors if the spectrum is sufficiently separated. A ratio can then be obtained to facilitate analysis. In another embodiment, a normalizing patch may be adjacent to provide a reference signal, thereby simplifying the calibration of the instrument.

BRIEF DESCRIPTION OF THE DRAWINGS

FIG. 4 is a cross sectional view of an interventional device fitted with a lysing core.

FIG. 5 is a side view of a secondary insertable device having a tip and a multifilar shaft.

FIG. 6 is a cross sectional view of a hollow needle carrying the readable polydeoxynucleotide array module equipped insertable appliance.

DETAILED DESCRIPTION OF THE DRAWINGS

Figure 1:
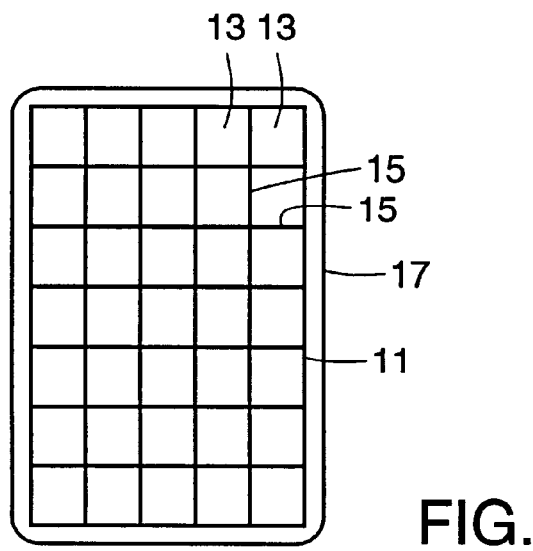
FIG. 1 is a planar view of a probe array containing a multiplicity of fluorescent probes on its surface.

Referring now to FIG. 1, the planar view of a probe array 11 is shown as a grid-like array with a plurality of chambers 13 arranged to have separators 15 within a frame 17. The frame 17 may be a small injection-molded component made of a plastic such as polystyrene or a molded material such as glass. The separators 15 may be molded integrally to the frame 17 or may be separate elements placed within it. The overall dimensions of the frame 17 may be small. Typical dimensions are less than 1 mm by 1 mm.

Figure 1A:
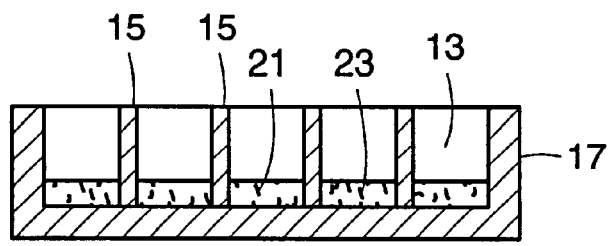
FIG. 1A is a cross sectional view of the probe array of FIG. 1.

Referring now to FIG. 1A, which is a cross sectional view of the probe array 11, the aforementioned separators 15 are effective to separate a fluorescent probe material 21 that may have different characteristics from an adjacent fluorescent probe material 23. Probe materials 21 and 23 are generally deposited in a thin layer on top of a substrate, in this case the material of the frame 17. Alternatively, the frame 17 may be made of a foraminous material or a partly foraminous substance such as sol gel (not shown). The probe materials may be incorporated into the substrate, which may be a flat surface which allows ink printing processes to be used to deposit the probe array materials at high speeds and at low cost.

Probe materials generally are engineered molecular materials that are designed to have an affinity to one or more constituents that may be expected to be found in the tissue, fluid or chemical mix to be analyzed. These probe materials may be made sensitive to specific genes or gene segments through complimentary genetic indicators that have been designed to fluoresce or change color, as observed by the naked eye or by spectrographic analysis methods, when they are linked to a molecule to which they have affinity. A large number of different types and combinations of optically readable probes are being manufactured today that have specific affinity to one or more genes, proteins or other chemicals. In preferred embodiments, the present invention contemplates the use of two classes of probes: (i) protein sensitive probes, such as GFP (green fluorescent probe) from the jellyfish *Aequorea Victoria*; and (ii) modified oligonucleotide probes that are fluorogenic, such as those manufactured by Synthegen LLC, Houston, Tex. 77042. Additional probes suited for use in the present invention are available from Midland Certified Reagent Company, Midland, Tex.

79701, and Transbio Corp., Baltimore, Md. 21220. Typically these probes must be used in vitro due to either their lack of biocompatability or because they must be used in conjunction with aggressive reagents that are toxic to cells.

Figure 1B:
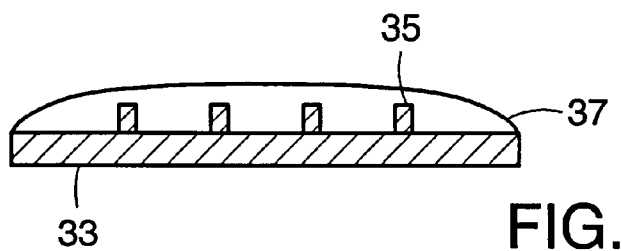
FIG. 1B is a cross sectional view of a sheet of material carrying a probe array.

Various methods and configurations may be used to deposit or arrange probe locations and positions in an array or singly. For instance, a sheet of plastic material 33, as shown in FIG. 1B, may have lines 35 made of probe filled ink printed in any arrangement that may be produced with printing methods. More than one type of probe-filled ink may be used to produce various patterns and arrangements, including overlapping patterns (not shown). The ink pattern lines 35 may be protected with a topcoat 37 which may be made of a dissolvable gel such as ordinary gelatin, or another material such as a soluble or even a waterproof polymer that only dissolves and provides access to the probe material in the probe-filled ink in lines 35 after the application of a solvent. The arrangement of the sensitive areas by this process allows the probe materials to be applied to a variety of surfaces and substrates, including medical devices such as needles, trocars, forceps, catheters, guidewires, implants and prostheses, in an inexpensive and reliable manner.

The following discussion and description of the present invention is directed to a readable polydeoxynucleotide array module (RPAM). However, those skilled in the art will appreciate that the present invention and specific embodiments described below may be utilized with any number of probe arrays and the RPAM described here is provided as only one, non-limiting, example.

Figure 2:
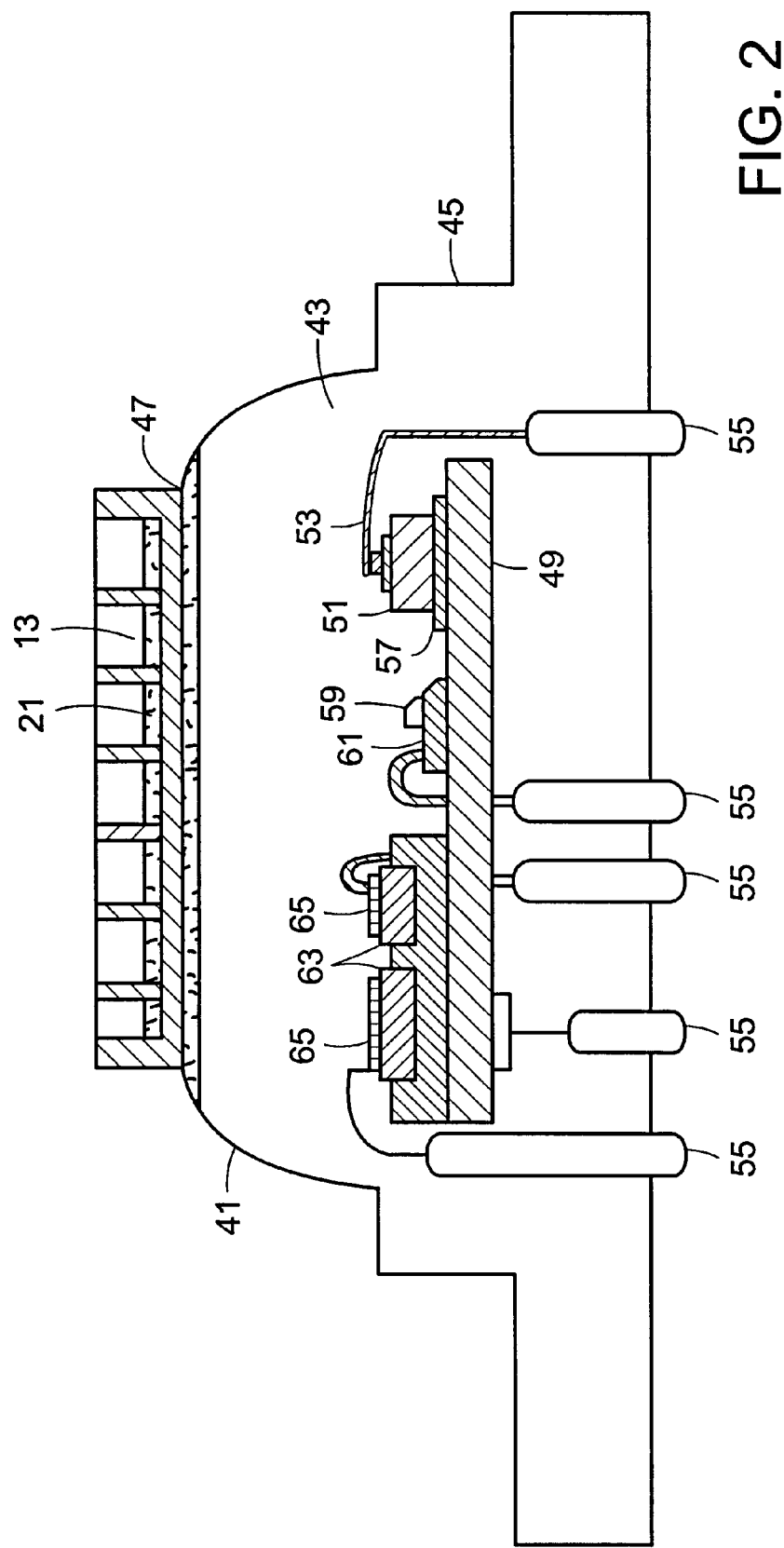
FIG. 2 is a cross-sectional view of a readable polydeoxynucleotide array module. (RPAM)

Referring now to FIG. 2, which is a cross sectional view of a readable polydeoxynucleotide array module (RPAM) 41, the probe array 11 may be positioned adjacent to a spectrometer module that is encapsulated in an at least partly transparent housing 45. The probe array 11 may be cemented to the side, top or other area within a spectrometer module 43 with an optical cement (not shown), or by a solvent bond line 47 which allows two plastics to be fused through partial melting. A spectrometer module suitable for use in this invention has been described in pending U.S. patent application Ser. No. 08/898,604, the entire disclosure of which is incorporated by reference herein.

Specifically, the spectrometer module used in the present invention includes a light source and a light detector for placement inside a body such that optical conduits are not necessary to deliver light signals to and from the RPAM inside the body. The miniature spectrometer includes the light source and one or more light detectors. The light source illuminates a tissue region and the light detectors detect optical properties of the illuminated tissue by measuring modified light signals. The light detectors convert optical signals to electrical signals such that one or more electrical wires placed inside an interventional device can deliver the electrical signals from the RPAM to a signal display or a microprocessor.

The light source and the light detectors are energized by an external power supply through electrical wires. In another embodiment, an optically transparent tip encapsulates a spectrometer. The tip is shaped to optimize tissue contact and optical transmission. The tip encapsulating the spectrometer is disposed at a distal end of an interventional device. The tip may be coated with a material to improve light transmission. The tip may include at least one fluid channel, which is in communication with a lumen inside the interventional device, to deliver a fluid to a tissue region. The spectrometer may also include a light source and the light detectors formed on a single substrate. The light source may be a light emitting diode and the light detectors may be a photodiode comprising multiple channels, where both devices are formed on a silicon substrate. The light detector can include multiple channels to detect light emission at multiple wavelengths.

Still referring to FIG. 2, probe array 11 may be integrally molded onto the surface of the spectrometer module 43 creating a somewhat simplified one-piece unit which may provide processing advantages in high speed production environments where parts counts are intentionally kept low to minimize stock and therefore reduce cost of fabrication and assembly. Injection molding or casting of the components is effective to produce miniature components that correspond in size to conventional silicon-based integrated circuit scale. Therefore it should be appreciated that the RPAM may be small, e.g., about the size of a miniature electronic component such as a surface mount device. Such devices include packaging, leads, and other components, and may be obtainable in size ranges of less than 1 mm in length. Such devices may typically be configured in the range from about 0.5 mm to about 3 mm to produce small, useful devices for in vivo use. The RPAM 41 may also have printable surfaces according to the construction of alternative probe array configurations as described in FIG. 1A and FIG. 1B, if desired. Referring once again to FIG. 2, the internal components of the RPAM consist of a substrate material 49 such as silicon upon which a light-emitting diode light source 51 is mounted with power lead 53 attached to one of terminals 55. Various colors and types of diode light sources may be used, including those now available that emit light in the infrared, the red, the yellow, the green, the blue, and the blue-violet regions. A working range of RPAM excitation wavelengths is from about 1100 nanometers to about 250 nanometers and may comprise monochromatic, bichromatic or broadband emissions. The exit aperture 57 is positioned to illuminate movable mirror 59 which is bonded to piezoelectric stack actuator 61. Empowerment of the stack actuator 61 is effective to direct light emission from diode light source 51 to one or more chambers 13. Light emission from the probe materials 21 is picked up by one or more light detectors 63 through filters 65. Signals from the detectors 63 are brought out from the RPAM through other terminals 55.

Figure 2A:
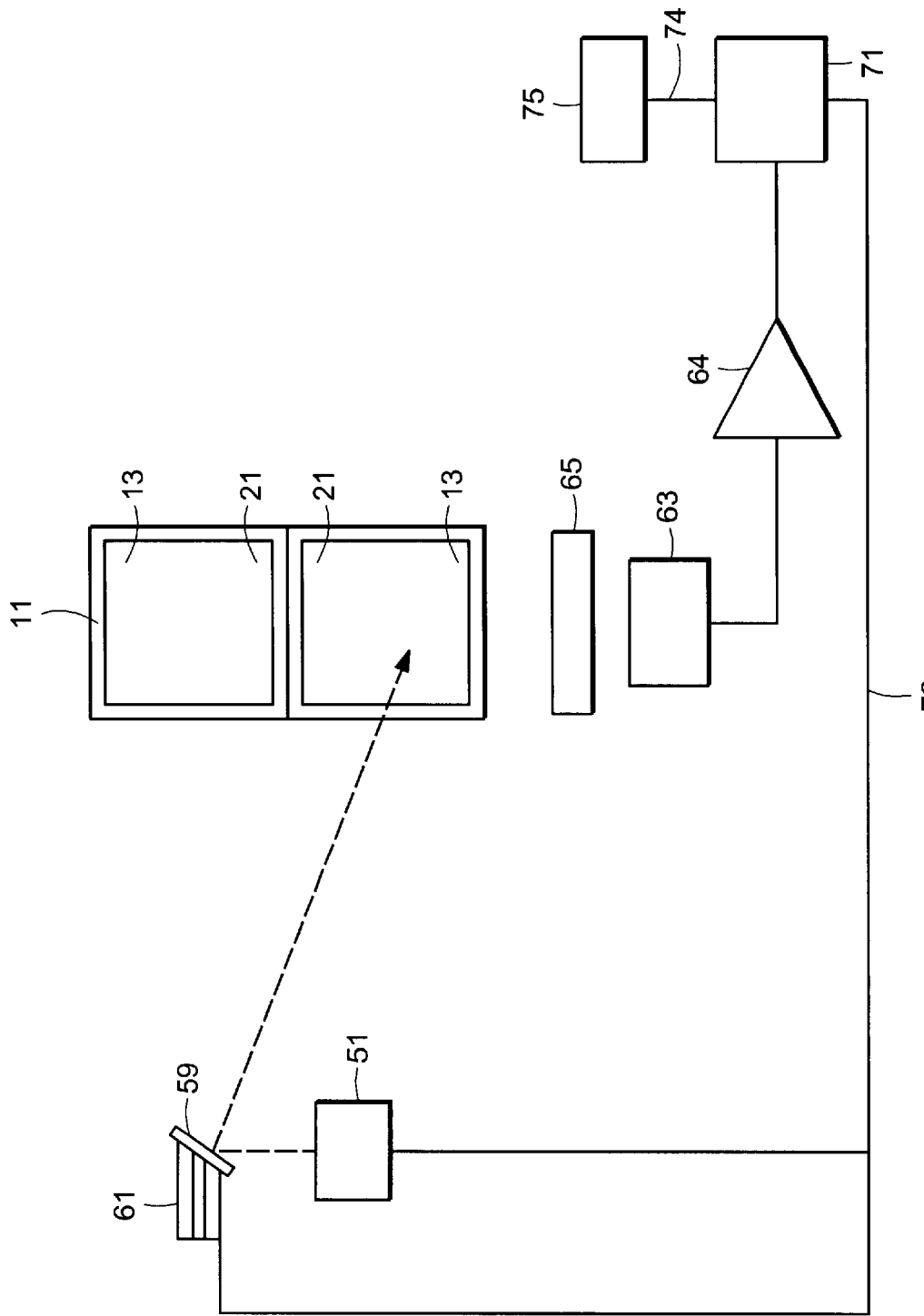
FIG. 2A is a block diagram of the readable polydeoxynucleotide array module and system.

Referring now to FIG. 2A, the operation of the RPAM is depicted in block diagram form as follows: Light is generated and directed from light source 51 and directed at one or more of chambers 13 by mirror 59, which impinges upon at least one probe material 21. Fluorescence or other secondary light generated by the action of the light energy upon the probe material causes a second emission that may be detected by one or more light detectors 63 after passing through a bandpass filter 65. The signal may be amplified and/or conditioned by one or more amplifier stages 64. Filters 65 allow the system to discriminate between various secondary light emission wavelengths, and signals from said light detectors 63 may be synchronized with the operation of light source 51 so that at any given time there is a known relationship between the particular probe that is illuminated and its response as detected by the light detectors. The timing and relationship of the light generating and light detecting event and the spatial position of the mirror 59, are controlled by CPU 71 and sent to the components via control lines 73.

The data obtained may be stored or presented in a display device or other therapeutic device which can be a graphical display, a television monitor, printout or drug delivery pump, interventional device, motor or actuator, etc. Accordingly, this apparatus may effectively scan or read a plurality of probe materials in a repeatable, fast and controllable manner, and the information read may be stored, displayed, or used to initiate another action such as a therapeutic application of a drug, or control of a motor. The bandpass filter system of detecting one or more light wavelengths for this purpose is basic and that more complex schemes could be employed by those of ordinary skill in the art. Such schemes may include, without limitation; light wavelength detection systems comprising gratings, graduated filters, heterodyne detection, acousto-optic tunable filtering, and other light detectors that effectively provide and amplitude and frequency responsive signal. A diffraction grating (not shown), for instance, may be attached to movable mirror 59 to provide spatial and chromatic control simultaneously.

Figure 3:
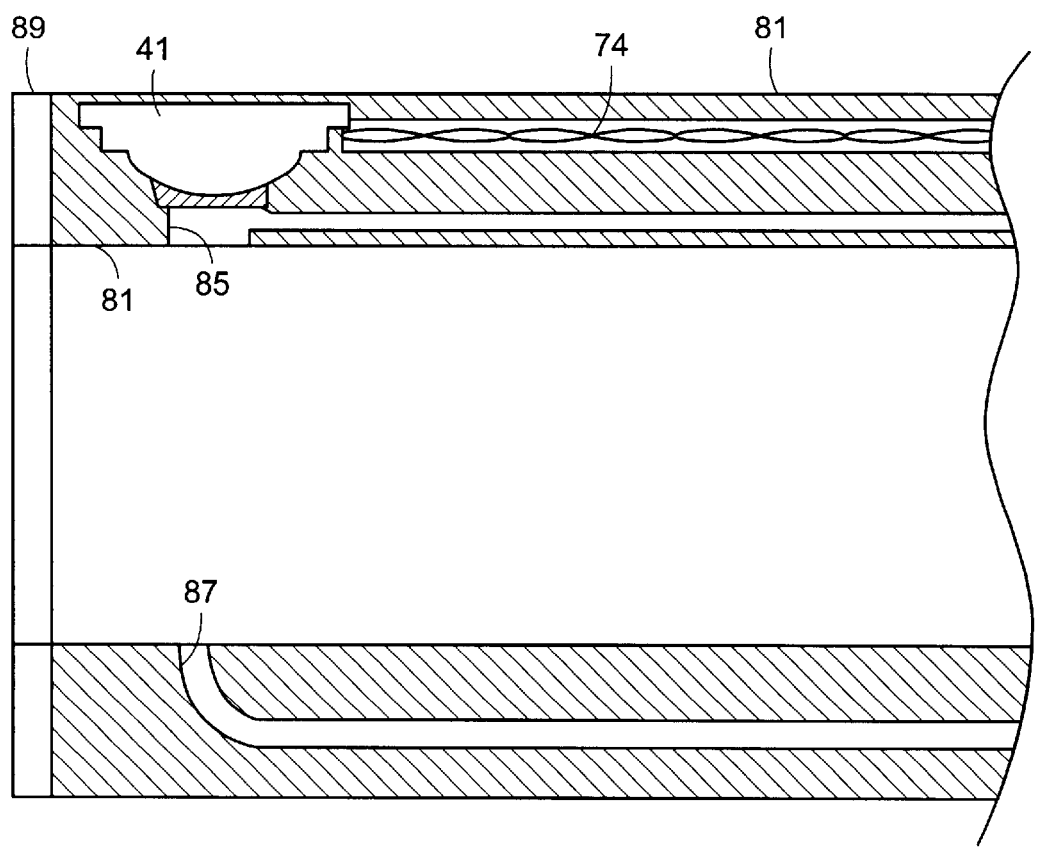
FIG. 3 is a cross sectional view of an interventional device carrying the readable polydeoxynucleotide array module.

Referring now to FIG. 3, the cross sectional view of an interventional device incorporating the spectrometer and probe still referred to here as RPAM 41; there is a primary insertable appliance 81 such as a catheter which may have a distal end and a proximal end and may consist of a plastic, rubber or metal material that is generally elongated in shape, has a small cross-section allowing it to pass easily through the body, and has one or more lumens or conduits which may extend through the length of the device. Shown in FIG. 3 is a device having three lumens although a greater or lesser number of lumens may be used depending upon the application for which the device is intended. The main lumen 83 is relatively large and is used to deliver a drug, a reagent, or a device to or beyond the distal tip 89. Suction lumen 85 is useful for drawing biological fluids, tissue or other materials into proximity with the RPAM 41, where the material can be analyzed. Signal wires 74 may extend to an external controller (not shown) or to a CPU, pump, motor or other controller as shown in FIG. 2A, 75.

Returning once again to FIG. 3, infusion lumen 87 may provide additional fluids, regents, drugs, wires or appliances that may be useful to the procedure. For example, the practitioner will appreciate that additional reagents can be introduced to facilitate analysis. Such additional reagents can include: denaturants, such as guanidinium thiosulfate; buffers, such as Tris-Cl; detergents, such as SDS; chelators, such as EDTA; enzymes, such as proteinases and/or DNAases; and other reagents known to those of ordinary skill in the art which may be appropriate to the particular analysis to be carried out using the apparatus of the present invention.

Referring now to FIG. 4, a cross sectional view of an interventional device such as a primary insertable appliance 81 fitted with a lysing core 101, is shown. The lysing core 101 utilizes mechanical motion to disrupt cells in order to make the cell contents available for analysis by the RPAM (not shown). The use of a lysing device in conjunction with the RPAM system eliminates the need for potentially toxic reagents that are commonly used to open cells in vitro. The lysing head 105 consists here of a more or less hemispherical component that may be comprised of a metal or plastic, which is mounted at the distal end of a driveshaft 103. Such driveshafts are well known for their ability to deliver torque and rotary motion from a proximal motor 107 or by hand control. As taught in this invention, motor 107 is one of a class of components shown in FIG. 2A as 75 which may be controlled by system CPU 71, also shown in FIG. 2A. Numerous other lysing devices are known that may abrade, disrupt, dissolve, pressurize, vacuum, cavitate or otherwise apply mechanical forces to a cell or cells that is effective to disrupt the cell and make its contents available for analysis. It should be pointed out that such damage to cells is usually minimized to avoid permanent damage to the organ, vessel, duct or tissue being tested. The lysing head 105 need not be relatively large and may be made small enough so that it may easily pass through the device from the proximal end so that another device or implant may be inserted, if needed, through the same large lumen 83. Such an implant may be a solid or porous, foraminous or dissolvable seed, implant, stent, gel or the like, which may carry therapeutic agents to a particular site in the body. This system provides the advantage that local conditions can be determined through use of the polydeoxynucleotide readable array (afforded by the construction of the RPAM device as described herein), and therefore, better and more precise application of appropriate medicaments, drugs, therapeutic genetically based substances, etc., is facilitated. Further advantages are provided in that the information is obtained at or near real time, and that information is obtainable from the exact location of a proposed therapeutic intervention. Such a device that may be used to place an implant is shown in FIG. 5, which is a side view of a secondary insertable device 111 comprising a rotary, multifilar flexible driveshaft 112 having a therapeutic tip 113 terminating in an anchoring device 115 shown as a screw form capable of being screwed into tissue until separable joint 117 breaks, after which the remaining part of insertable device 111 may be withdrawn. Driveshaft 112 may be hollow, to allow tether 119 to remain attached to therapeutic tip 113. Tether material may be constructed of a wire to allow the sending and receiving of an electrical signal, or may simply be used as a retrieval device to retrieve any portion of the therapeutic tip that may remain after the need for it is over.

Numerous carrying devices may be used to deliver the RPAM. FIG. 6 is a cross sectional view of a hollow needle 121 carrying the RPAM insertable appliance 81. The advantage of a needle is that it allows the introduction of the RPAM into portions of the body where there is no natural passageway. This method allows the user to position the distal tip of the lysing head 105 in various positions with respect to the sharp needle tip 106. The needle may be of stainless steel and may be inserted into body tissue such as muscle, breast, prostate, or cardiac tissue. The needle may be left in place, and the RPAM withdrawn temporarily to allow another appliance (not shown) to be introduced. Other carrying devices may include guidewires, balloon catheters, ultrasound catheters with both imaging or non-imaging, and rotatable or array configurations, introducer sheaths, balloon angioplasty catheters for use in the blood vessels of the heart, the extremities, and the vascular system, atherectomy catheters, and many other types of interventional devices, as well as intraoperative devices. The device of the invention may be used anywhere there is the need for fast, precise localized detection and analysis of nucleotides, proteins or the like, either for diagnostic purposes, or to guide therapy which itself may be made more localized, and therefore site-specific. Such uses are economical and have less impact on surrounding tissue that is free of disease. The invention allows use of any agent that may change color as a result of the application of a local chemical to be read and includes without limitation such agents as litmus, photodynamic therapeutic agents such as photofrin, fluorescent agents or dyes, staining dyes, luciferin, etc. The present invention permits analysis in a real time fashion without the need to remove and transport tissue specimens for later analysis.

What is claimed is:

1. An apparatus comprising:

an excitation source;

at least one optically detectable probe directed to an analyte, said probe attached to a substrate and situated to contact said analyte, wherein said probe is mixed with an ink to form a probe-filled ink and wherein said probe-filled ink is deposited upon said substrate;

a detector for detecting optical properties of said probe, said detector for converting optical signals representative of the detected optical properties to electrical signals;

wherein said excitation source, said probe, and said detector are adapted for placement together in an area of interest within a body.

2. The apparatus of claim 1 wherein said substrate comprises a sheet of plastic material.

3. The apparatus of claim 1 wherein a plurality of probe-filled inks are deposited upon said substrate in a specific ink pattern.

4. The apparatus of claim 3 wherein said ink pattern is protected by a topcoat.

5. The apparatus of claim 4 wherein said topcoat comprises a dissolvable gel.

6. The apparatus of claim 4 wherein said topcoat comprises a polymer material dissolvable only upon application of a solvent.

7. The apparatus of claim 1, wherein said excitation source, said probe, and said detector are disposed within a body-insertable device that is to be positioned in an area of interest within a body.

8. The apparatus of claim 7, wherein said body-insertable device is delivered to the area of interest by a carrying device.

9. The apparatus of claim 8, wherein said carrying device is selected from the group consisting of a hollow needle, a guide wire, a balloon catheter, an ultrasound catheter, an introducer sheath, and a balloon angioplasty catheter.

10. The apparatus of claim 7 wherein said body-insertable device comprises a catheter.

11. An apparatus comprising:

an excitation source;

at least one optically detectable probe directed to an analyte, said probe situated to contact said analyte;

a detector for detecting optical properties of said probe, said detector for converting optical signals representative of the detected optical properties to electrical signals;

wherein said excitation source, said probe, and said detector are disposed within a body-insertable device that is to be positioned in an area of interest within a body, said body-insertable device comprising a lumen positioned such that said lumen is capable of introducing to said area of interest a lysing system.

12. The apparatus of claim 11 wherein said lysing system comprises an ultrasonic transducer capable of rupturing cell membranes.

13. The apparatus of claim 11 wherein said lysing system comprises a pressurization and evacuation system capable of rupturing a cell membrane.

14. The apparatus of claim 11 wherein said lysing system comprises a mechanical lysing device.

15. The apparatus of claim 14 wherein said mechanical lysing device comprises a lysing head mounted at the distal end of a driveshaft.

16. The apparatus of claim 15 wherein said driveshaft delivers torque and rotary motion to said lysing head from a proximal motor.

17. The apparatus of claim 11 wherein said body-insertable device comprises an implantable device.

18. The apparatus of claim 17 wherein said implantable device comprises a rotary flexible driveshaft having a therapeutic tip terminating in an anchoring device.

19. The apparatus of claim 18 wherein said implantable device further comprises a separable joint between said therapeutic tip such that said therapeutic tip remains within a body after removal of said body-insertable device.

20. The apparatus of claim 19 further comprising a tether such that said tether remains attached to said therapeutic tip after removal of said body-insertable device.

21. The apparatus of claim 20 wherein said tether is capable of transmitting an electrical signal.

22. The apparatus of claim 11 wherein said body-insertable device is delivered to the area of interest by a carrying device.

23. The apparatus of claim 22 wherein said carrying device is selected from the group consisting of a hollow needle, a guide wire, a balloon catheter, an ultrasound catheter, an introducer sheath, and a balloon angioplasty catheter.

24. The apparatus of claim 11 wherein said body-insertable device comprises a catheter.

* * * * *